United States Patent [19]

Ogawa et al.

[11] Patent Number: 5,538,974
[45] Date of Patent: Jul. 23, 1996

[54] OPHTHALMIC COMPOSITION FOR LOWERING INTRAOCULAR PRESSURE

[75] Inventors: Takahiro Ogawa, Nishinomiya; Takaaki Deguchi, Kobe, all of Japan

[73] Assignee: Senju Pharamceutical Co., Ltd., Osaka, Japan

[21] Appl. No.: 378,244

[22] Filed: Jan. 24, 1995

[30] Foreign Application Priority Data

Jan. 27, 1994 [JP] Japan ................................. 6-007470

[51] Int. Cl.⁶ ...................... A61K 31/495; A61K 31/39
[52] U.S. Cl. ................................. 514/253; 514/431
[58] Field of Search ............................. 514/431, 253

[56] References Cited

FOREIGN PATENT DOCUMENTS

| 0145494 | 6/1985 | European Pat. Off. . |
| 0229467 | 7/1987 | European Pat. Off. . |

OTHER PUBLICATIONS

Mermoud et al., KLIN. MBL. AUGENHEICK, vol. 198 (1991) pp. 332–334.
Mermoud et al., Ophtalmologie, vol. 6 (1992) pp. 411–413.
Chang et al, *Medline Abstracts*, abstract #89124670, 1985.
Krootila et al., *Chemical Abstracts*, vol. 108, No. 17, abstract #143438h, p. 76, 1988.

*Primary Examiner*—Marianne M. Cintins
*Assistant Examiner*—William A. Jarvis
*Attorney, Agent, or Firm*—Wenderoth, Lind & Ponack

[57] ABSTRACT

An ophthalmic composition comprising a compound of the formula

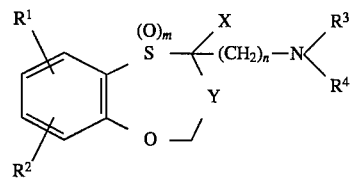

wherein $R^1$ and $R^2$ are each a hydrogen, a halogen, a hydroxyl, a lower alkyl or a lower alkoxy, $R^3$ and $R^4$ are each a hydrogen, an optionally substituted lower alkyl, an optionally substituted cycloalkyl or an optionally substituted aralkyl, or form, together with the adjacent nitrogen atom, an optionally substituted ring, X is a hydrogen, an optionally substituted lower alkyl, an optionally substituted aryl or an optionally esterified or amidized carboxyl, Y is >C=O or >CH—OR⁵ wherein $R^5$ is a hydrogen, an acyl or an optionally substituted carbamoyl, m is an integer of from 0 to 2, and n is an integer of from 1 to 6, or a salt thereof, and a method for the treatment of glaucoma, comprising administering said compound or a salt thereof.

7 Claims, 1 Drawing Sheet

OPHTHALMIC COMPOSITION FOR LOWERING INTRAOCULAR PRESSURE

FIELD OF THE INVENTION

The present invention relates to an ophthalmic composition comprising a 1,5-benzoxathiepine derivative having a superior local action, and a method for the prevention and treatment of eye diseases, comprising administering said derivative.

BACKGROUND OF THE INVENTION

Glaucoma, a pathologic state in which intraocular pressure exceeding the normal range of 10–20 mmHg results in eyesight disorder, is among the intractable ophthalmopathies. The current therapy for glaucoma is to lower intraocular pressure. For glaucoma chemotherapy, choline agonists, represented by pilocarpine, and anti-choline esterase agents have long been used as eyedrops. These drugs, however, cause severe side effects such as a sensation of darkness due to miosis, eye injection and other symptoms, as well as iridic cystoma, iris synechia, cataract and retinal detachment when used in long-term continuous administration. Although sympathetic nerve agonists such as epinephrine and dipivefrine have been used for their ocular hypotensive action, their use is limited to open-angle glaucoma, and can cause mydriasis, blepharitis and conjunctival pigmentation, and systemic symptoms such as increased heart rate and hypertension. In recent years, β-blockers such as timolol, pindolol and carteolol have been widely used, since they are advantageous in that their instillation suppresses aqueous humor production and lowers ocular tension, without acting on the pupil. These drugs, however, tend to cause local symptoms such as feeling of eye dryness, allergic blepharitis and superficial keratitis. The only group of ocular hypotensive agents that can be used systemically in long-term continuous administration is carbonic anhydrase inhibitors such as acetazolamide and metazolamide, but these can cause gastrointestinal disorder, ureteroliths and electrolytic anomalies. In recent years, angiotensinconverting enzyme inhibitors, which inhibit the reninangiotensin system involved in blood pressure regulation, and angiotensin II antagonists have been reported to be useful as glaucoma remedies, but none have seen practical application.

Recently, ketanserin, which selectively blocks a serotonin (5-HT$_2$) receptor and is represented by the formula

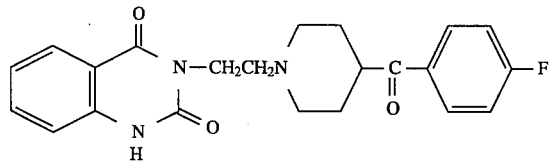

has been reported to simultaneously lower intraocular pressure of both eyes when administered to one eye [JOURNAL OF OCULAR PHARMACOLOGY, Vol. 3, No. 4, pp 279–291 (1987)].

EP-A-145494 and U.S. Pat. No. 4751316 teach that a compound having a completely different chemical structure from ketanserin, which is represented by the formula

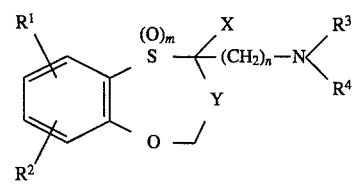

wherein $R^1$ and $R^2$ are each hydrogen, halogen, hydroxyl, lower alkyl or lower alkoxy, $R^3$ and $R^4$ are each hydrogen, optionally substituted lower alkyl, optionally substituted cycloalkyl or optionally substituted aralkyl, or form, together with the adjacent nitrogen atom, an optionally substituted ring, X is hydrogen, optionally substituted lower alkyl, optionally substituted aryl or optionally esterified or amidized carboxyl, Y is >C=O or >CH—OR$^5$ wherein $R^5$ is hydrogen, acyl or optionally substituted carbamoyl, m is an integer of from 0 to 2, and n is an integer of from 1 to 6, and a salt thereof have superior serotonin S$_2$ receptor blocking action, calcium antagonistic action, cerebrovascular contraction remisslye action, renal circulation improving action, diuretic action and antithrombogenic action and are useful for the prevention and treatment of ischemic heart diseases such as angina pestoris and cardiac infarction, thrombus, hypertension, and cerebrocircular disorders such as cerebrovascular contraction and transient ischemic attack. However, no ophthalmic action, particularly local ophthalmic action, of these compounds has been reported.

When developing an ophthalmic agent, attention should be paid to the manifestation of efficacy only in the instillation site, which avoids passage through the systemic circulatory system or the central nervous system, namely, exertion of local action, and it is desirable that the agent does not exert influences on any other part besides the target lesion, or systemic influences. Accordingly, there is a demand for the development of an ophthalmic agent which has a local action, causes less side effects, and can be used safely.

SUMMARY OF THE INVENTION

The present inventors have now found that a compound of the formula

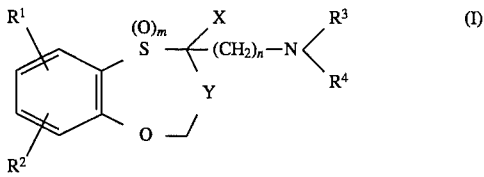

(I)

wherein $R^1$ and $R^2$ are each a hydrogen, a halogen, a hydroxyl, a lower alkyl or a lower alkoxy, $R^3$ and $R^4$ are each a hydrogen, an optionally substituted lower alkyl, an optionally substituted cycloalkyl or an optionally substituted aralkyl, or form, together with the adjacent nitrogen atom, an optionally substituted ring, X is a hydrogen, an optionally substituted lower alkyl, an optionally substituted aryl or an optionally esterified or amidized carboxyl, Y is >C=O or >CH—OR$^5$ wherein $R^5$ is a hydrogen, an acyl or an optionally substituted carbamoyl, m is an integer of from 0 to 2, and n is an integer of from 1 to 6 [hereinafter referred to as Compound (I)] and a salt thereof are not greatly influenced by the kind of $R^1$, $R^2$, $R^3$, $R^4$, X, m or n, can be used as ophthalmic agents, exert a local action, particularly, a superior intraocular pressure lowering action, scarcely show side effects in a long-term use, and can be used safely as ophthalmic agents.

3

Accordingly, the present invention provides:

(1) an ophthalmic composition containing a Compound (I) or a salt thereof;

(2) an ocular hypotensive composition containing a Compound (I) or a salt thereof;

(3) the ocular hypotensive composition of (2) above, containing a compound of the formula

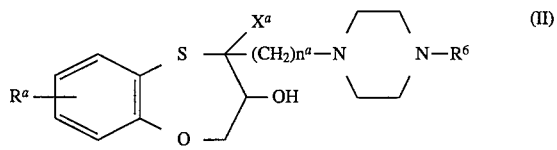
(II)

wherein $R^6$ is an optionally substituted phenyl, $R^a$ is a lower alkoxy, $X^a$ is a lower alkoxycarbonyl and $n^a$ is an integer of from 2 to 4 [hereinafter referred to as Compound (II)] or a salt thereof;

(4) the ocular hypotensive composition of (3) above, wherein the lower alkoxy is methoxy;

(5) the ocular hypotensive composition of (3) above, wherein the lower alkoxycarbonyl is methoxycarbonyl;

(6) the ocular hypotensive composition of (3) above, wherein $R^6$ is a phenyl;

(7) the ocular hypotensive composition of (3) above, wherein $n^a$ is 3;

(8) the ocular hypotensive composition of (2) above, containing methyl cis-3-hydroxy-7-methoxy-4-[3-(4-phenyl-1-piperazinyl)propyl]-3,4-dihydro-2H-1,5-benzoxathiepine-4-carboxylate (hereinafter referred to as Compound A) or a salt thereof;

(9) a method for preventing and treating eye diseases, comprising administering a pharmaceutically effective amount of a Compound (I) or a salt thereof;

(10) a method for lowering intraocular pressure, comprising administering a pharmaceutically effective amount of a Compound (I) or a salt thereof;

(11) the method of (10) above, comprising administering a pharmaceutically effective amount of a Compound (II) or a salt thereof;

(12) the method of (11) above, wherein the lower alkoxy is methoxy;

(13) the method of (11) above, wherein the lower alkoxycarbonyl is methoxycarbonyl;

(14) the method of (11) above, wherein $R^6$ is a phenyl;

(15) the method of (11) above, wherein $n^a$ is 3; and

(16) the method of (10) above, comprising administering Compound A or a salt thereof.

DETAILED DESCRIPTION OF THE INVENTION

Figure 1:
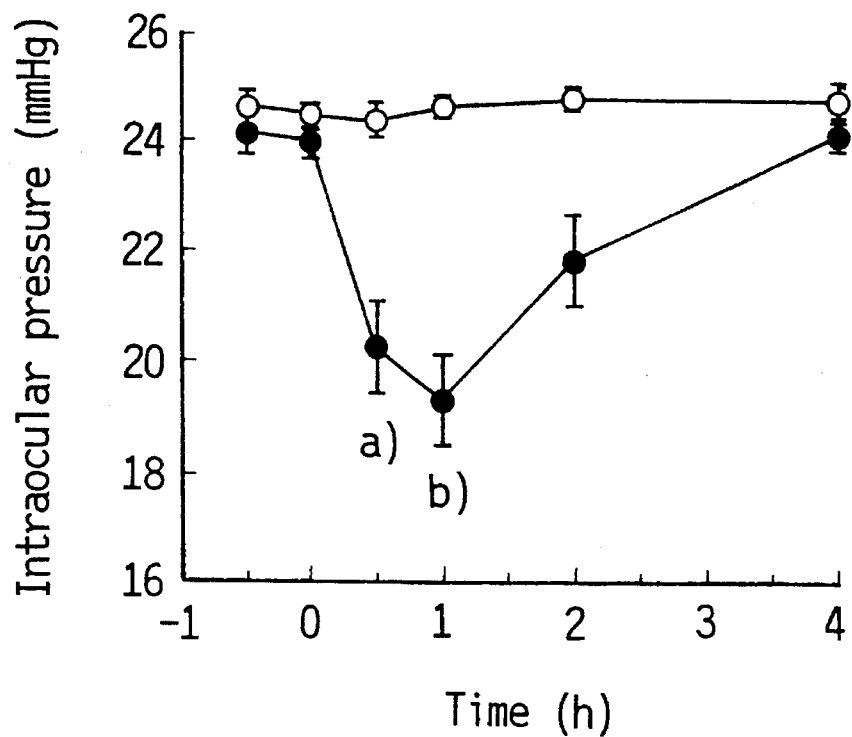
FIG. 1 is a graph showing the time-course changes in the intraocular pressure of the eye, which received instillation of a test drug, of pigmented rabbits.

In the above formulas, $R^1$ and $R^2$ are each hydrogen, halogen, hydroxyl, lower alkyl or lower alkoxy.

4

Examples of the halogen represented by $R^1$ and $R^2$ are fluorine, chlorine, bromine and iodine. Examples of the lower alkyl represented by $R^1$ and $R^2$ include alkyl having 1 to 6 carbon atoms, such as methyl, ethyl, propyl, isopropyl, butyl, sec-butyl and tert-butyl. Examples of the lower alkoxy represented by $R^1$ and $R^2$ include alkoxy having 1 to 6 carbon atoms, such as methoxy, ethoxy, propoxy, isopropoxy, butoxy, isobutoxy, sec-butoxy and tert-butoxy. One of $R^1$ and $R^2$ is preferably hydrogen and the other is preferably lower alkoxy, with more preference given to a lower alkoxy bonded to the 7-position of the benzoxathiepine skeleton.

$R^3$ and $R^4$ are each hydrogen, optionally substituted lower alkyl, optionally substituted cycloalkyl or optionally substituted aralkyl, or $R^3$ and $R^4$ combinedly form, together with the adjacent nitrogen atom, an optionally substituted ring.

Examples of the lower alkyl represented by $R^3$ and $R^4$ include alkyl having 1 to 6 carbon atoms, such as methyl, ethyl, propyl, isopropyl, butyl, isobutyl, sec-butyl and tert-butyl. The lower alkyl may be substituted, at (a) substitutable position(s), by one or two substituents selected from $C_3$–$C_8$ cycloalkyl (e.g. cyclopropyl, cyclobutyl, cyclopentyl, cyclohexyl, cycloheptyl and cyclooctyl), halogen (e.g. fluorine, chlorine, bromine and iodine), hydroxyl, lower ($C_1$–$C_4$) alkoxy (e.g. methoxy, ethoxy, propoxy and butoxy), lower ($C_1$–$C_5$) alkanoyloxy (e.g. acetoxy, propionyloxy, butyryloxy and pivaloyloxy), mono- or di-lower ($C_1$–$C_4$) alkylamino (e.g. methylamino, dimethylamino and methylethylamino), $C_3$–$C_8$ cycloalkylamino (e.g. cyclopentylamino and cyclohexylamino), lower ($C_1$–$C_5$) alkanoylamino (e.g. acetamido and propionamido), benzamido, lower ($C_1$–$C_4$) alkylthio (e.g. methylthio, ethylthio, propylthio and butylthio), carbamoyl, N-lower ($C_1$–$C_4$) alkylcarbamoyl (e.g. methylcarbamoyl and ethylcarbamoyl), N,N-di-lower ($C_1$–$C_4$) alkylcarbamoyl (e.g. dimethylcarbamoyl, diethylcarbamoyl and methylethylcarbamoyl) and the like.

Examples of the cycloalkyl represented by $R^3$ and $R^4$ include cycloalkyl having 3 to 8 carbon atoms, such as cyclopropyl, cyclobutyl, cyclopentyl, cyclohexyl, cycloheptyl and cyclooctyl. The cycloalkyl may be substituted, at (a) substitutable position(s), by one to four substituents selected from lower ($C_1$–$C_4$) alkyl (e.g. methyl, ethyl, propyl and butyl), lower ($C_1$–$C_4$) alkoxy (e.g. methoxy, ethoxy, propoxy, isopropoxy and butoxy), lower ($C_1$–$C_5$) alkanoylamino (e.g. acetamido), hydroxyl and the like.

Examples of the aralkyl represented by $R^3$ and $R^4$ include phenyl-lower ($C_1$–$C_4$) alkyl, such as benzyl, phenethyl, 3-phenylpropyl, α-methylbenzyl, α-ethylbenzyl, α-methylphenethyl, β-methylphenethyl and β-ethylphenethyl. The phenyl in these aralkyls may be substituted, at (a) substitutable position(s), by one to three substituents selected from halogen (e.g. fluorine, chlorine, bromine and iodine), lower ($C_1$–$C_4$) alkyl (e.g. methyl, ethyl, propyl and butyl), lower ($C_1$–$C_4$) alkoxy (e.g. methoxy, ethoxy, propoxy, isopropoxy and butoxy), methylenedioxy, amino, nitro, hydroxyl and the like. Examples of the substituted aralkyl are 2-(4-chlorophenyl)ethyl, 2-(4-hydroxyphenyl)ethyl, 2-(4methoxyphenyl)ethyl, 2-(3,4-dimethoxyphenyl)ethyl, 2-(3,4,5trimethoxyphenyl)ethyl, 2-(3,4-methylenedioxyphenyl)ethyl, 2-(p-tolyl)ethyl, 3,4-dimethoxybenzyl, 3,4-methylenedioxybenzyl, 3,4,5-trimethoxybenzyl, 4-ethylbenzyl and 4-chlorobenzyl.

The ring which is combinedly formed by $R^3$ and $R^4$ together with the adjacent nitrogen atom is, for example, cyclic amino which may have a hetero atom, such as nitrogen, oxygen and sulfur, besides the nitrogen atom. Examples of the ring include 5 to 7-membered cyclic aminos, such as pyrrolidinyl, morpholinyl, piperidyl, piperazinyl and homopiperazinyl. The cyclic amino may have 1 to 4 substituents at (a) substitutable position(s), and such substituents are exemplified by lower ($C_1$–$C_4$) alkyl (e.g. methyl, ethyl, propyl and butyl), aryl, aralkyl, acyl and heterocyclic groups. The aryl as a substituent for the cyclic amino is, for example, $C_6$–$C_{10}$ aryl such as phenyl. The aryl may be substituted, at (a) substitutable position(s), by one to three substituents selected from halogen (e.g. fluorine, chlorine, bromine and iodine), lower ($C_1$–$C_4$) alkyl (e.g. methyl, ethyl, propyl and butyl), lower ($C_1$–$C_4$) alkoxy (e.g. methoxy, ethoxy, propoxy, isopropoxy and butoxy), methylenedioxy, amino, nitro, hydroxyl and the like. Examples of the aralkyl as a substituent for the cyclic amino include phenyl-lower ($C_1$–$C_4$) alkyl, such as benzyl and phenethyl, diphenyl-lower ($C_1$–$C_4$) alkyl, such as benzhydryl, and triphenyl-lower ($C_1$–$C_4$) alkyl. Examples of the acyl as a substituent for the cyclic amino include acyl derived from lower ($C_1$–$C_4$) aliphatic carboxylic acid, such as lower ($C_1$–$C_4$) alkanoyl (e.g. acetyl, propionyl and butyryl), and acyl derived from aromatic carboxylic acid, such as benzoyl, phenyl-lower ($C_1$–$C_4$) alkanoyl (e.g. phenylacetyl) and phenyl-lower ($C_1$–$C_4$) alkenoyl (e.g. cynnamoyl). The phenyl of the aralkyl and the acyl derived from aromatic carboxylic acid as a substituent for the cyclic amino may be substituted, at (a) substitutable position(s), by one to three substituents selected from halogen (e.g. fluorine, chlorine, bromine and iodine), lower ($C_1$–$C_4$) alkyl (e.g. methyl, ethyl, propyl and butyl), lower ($C_1$–$C_4$) alkoxy (e.g. methoxy, ethoxy, propoxy, isopropoxy and butoxy), methylenedioxy, amino, nitro, hydroxyl and the like. Examples of the heterocyclic group as a substituent for the cyclic amino include 5 to 7-membered rings having 1 to 3 nitrogen atoms, such as pyrrolyl, pyrazolyl, imidazolyl, pyridyl, pyrimidinyl, pyridazinyl, triazinyl and azepinyl.

$R^3$ and $R^4$ preferably combinedly form, together with the adjacent nitrogen atom, a ring substituted by aryl, with more preference given to piperazinyl substituted by one aryl.

X is hydrogen, optionally substituted lower alkyl, optionally substituted aryl, or optionally esterified or amidized carboxyl.

The lower alkyl represented by X is, for example, an alkyl having 1 to 6 carbon atoms, such as methyl, ethyl, propyl, isopropyl, butyl, isobutyl, sec-butyl and tert-butyl. The lower alkyl may be substituted, at (a) substitutable position(s), by one or two substituents, such as oxo, hydroxyl, acyloxy and aryl. Examples of the lower alkyl substituted by oxo include lower ($C_1$–$C_4$) alkanoyl, such as acetyl, propionyl and butyryl. Examples of the lower alkyl substituted by hydroxyl include hydroxymethyl. The acyl of the acyloxy is, for example, an acyl derived from lower fatty acid, such as lower ($C_1$–$C_5$) alkanoyl (e.g. acetyl, propionyl and butyryl). Examples of the lower alkyl substituted by acyloxy include acetyloxymethyl, propionyloxymethyl and butyryloxymethyl. The lower alkyl substituted by aryl is, for example, a lower ($C_1$–$C_4$) alkyl substituted by phenyl, such as benzyl, and the phenyl may be substituted, at (a) substitutable position(s), by one to three substituents selected from halogen (e.g. fluorine, chlorine, bromine and iodine), lower ($C_1$–$C_4$) alkyl (e.g. methyl, ethyl, propyl and butyl), lower ($C_1$–$C_4$) alkoxy (e.g. methoxy, ethoxy, propoxy, isopropoxy and butoxy), methylenedioxy, amino, nitro, hydroxyl and the like.

Examples of the aryl represented by X include $C_6$–$C_{10}$ aryl such as phenyl, and the aryl may be substituted, at (a) substitutable position(s), by one to three substituents selected from halogen (e.g. fluorine, chlorine, bromine and iodine), lower ($C_1$–$C_4$) alkyl (e.g. methyl, ethyl, propyl and butyl), lower ($C_1$–$C_4$) alkoxy (e.g. methoxy, ethoxy, propoxy, isopropoxy and butoxy), methylenedioxy, amino, nitro, hydroxyl and the like.

The esterified carboxyl represented by X include, for example, lower ($C_1$–$C_4$) alkoxycarbonyl, such as methoxycarbonyl, ethoxycarbonyl, propoxycarbonyl, isopropoxycarbonyl, butoxycarbonyl, isobutoxycarbonyl, sec-butoxycarbonyl and tertbutoxycarbonyl, and phenyl-lower ($C_1$–$C_4$) alkoxycarbonyl such as benzyloxycarbonyl.

The amidized carboxyl represented by X include, for example, carbamoyl, and the amino of the carbamoyl may be substituted by 1 or 2 lower ($C_1$–$C_4$) alkyl (e.g. methyl and ethyl), phenyl, phenyl-lower ($C_1$–$C_4$) alkyl (e.g. benzyl) and the like.

X is preferably an esterified carboxyl, with more preference given to a lower ($C_1$–$C_4$) alkoxycarbonyl.

$R^5$ is hydrogen, acyl or optionally substituted carbamoyl.

Examples of the acyl represented by $R^5$ include lower alkanoyl having 1 to 6 carbon atoms, such as acetyl, propionyl, butyryl, valeryl and pivaloyl, and phenyl-lower ($C_1$–$C_6$) alkanoyl derived from aromatic carboxyic acid, such as benzoyl, phenylacetyl and phenylpropionyl. The phenyl of the phenyl-lower ($C_1$–$C_6$) alkanoyl may be substituted, at (a) substitutable position(s), by one to three substituents selected from halogen (e.g. fluorine, chlorine, bromine and iodine), lower ($C_1$–$C_4$) alkyl (e.g. methyl, ethyl, propyl and butyl), lower ($C_1$–$C_4$) alkoxy (e.g. methoxy, ethoxy, propoxy, isopropoxy and butoxy), methylenedioxy, amino, nitro, hydroxyl and the like.

The amino of the carbamoyl represented by $R^5$ may be substituted by lower ($C_1$–$C_4$) alkyl (e.g. methyl, ethyl, propyl and butyl), phenyl, phenyl-lower ($C_1$–$C_4$) alkyl (e.g. benzyl and phenethyl) and the like. Such phenyl and the phenyl of the phenyl-lower ($C_1$–$C_4$) alkyl may be substituted, at (a) substitutable position(s), by one to three substituents selected from halogen (e.g. fluorine, chlorine, bromine and iodine), lower ($C_1$–$C_4$) alkyl (e.g. methyl, ethyl, propyl and butyl), lower ($C_1$–$C_4$) alkoxy (e.g. methoxy, ethoxy, propoxy, isopropoxy and butoxy), methylenedioxy, amino, nitro, hydroxyl and the like.

Y is preferably hydroxymethylene.

The sulfur atom in the formulas forms sulfide, sulfoxide or sulfone according to the integer of m, with preference given to the case where m is 0.

—$(CH_2)_n$— in the formula forms methylene, ethylene, trimethylene, tetramethylene, pentamethylene or hexamethylene, with preference given to trimethylene.

$R^6$ is optionally substituted phenyl. It is preferable that the phenyl represented by $R^6$ be not substituted. However, it may be substituted, at (a) substitutable position(s), by one to three substituents selected from halogen (e.g. fluorine, chlorine, bromine and iodine), lower ($C_1$–$C_4$) alkyl (e.g. methyl, ethyl, propyl and butyl), lower ($C_1$–$C_4$) alkoxy (e.g. methoxy, ethoxy, propoxy, isopropoxy and butoxy), methylenedioxy, amino, nitro, hydroxyl and the like.

$R^a$ is lower alkoxy. Examples of the lower alkoxy represented by $R^a$ include alkoxy having 1 to 6 carbon atoms, such as methoxy, ethoxy, propoxy, isopropoxy, butoxy, isobutoxy, sec-butoxy and tert-butoxy. $R^a$ is preferably methoxy and more preferably methoxy bonded to the 7-position of the benzoxathiepine skeleton.

$X^a$ is lower alkoxycarbonyl. Examples of the lower alkoxycarbonyl include lower ($C_1$–$C_4$) alkoxycarbonyl, such as methoxycarbonyl, ethoxycarbonyl, propoxycarbonyl, isopropoxycarbonyl, butoxycarbonyl, isobutoxycarbonyl, secbutoxycarbonyl and tert-butoxycarbonyl. $X^a$ is more preferably methoxycarbonyl.

$-(CH_2)n^a-$ in the formula forms ethylene, trimethylene or tetramethylene depending on the value of $n^a$, with preference given to trimethylene.

The salts of the compounds of the formulas (I) and (II) include, for example, pharmacologically acceptable salts with inorganic acids, such as hydrochloride, hydrobromide, sulfate, nitrate and phosphate, and salts with organic acids, such as acetate, tartrate, citrate, fumarate, maleate, toluenesulfonate and methanesulfonate, with preference given to hydrochloride.

Preferable example of Compound (I) is Compound (II).

Preferable example of Compound (II) is methyl cis-3-hydroxy-7-methoxy-4-[3-(4-phenyl-1-piperazinyl)propyl]-3,4-dihydro-2H-1,5-benzoxathiepine-4-carboxylate, Compound (A).

Compounds (I) and (II) have isomers with regard to asymmetric carbon atom. In the present invention, both racemates and optically active compounds are usable, and beneficial results may be achieved by using an optically active compound.

Compound (I) and a salt thereof can be produced by a method described in, for example, EP-A-145494 and U.S. Pat. No. 4,751,316, or an analogous method.

The ophthalmic composition of the present invention can be obtained by using a Compound (I) or a salt thereof.

While the amount of Compound (I) or a salt thereof varies depending on preparation forms, it is generally contained in a proportion of 0.02–2.0% by weight, preferably 0.05–1.0% by weight of the entire preparation.

The ophthalmic composition of the present invention preferably contains known additives generally used for ophthalmic agents, such as preservatives, isotonizing agents, buffers, stabilizers, thickeners and suspending agents. Examples of the preservative include p-hydroxybenzoates such as methyl p-hydroxybenzoate and propyl p-hydroxybenzoate, inverted soaps such as benzalkonium chloride, benzethonium chloride, chlorhexidine gluconate and cetylpyridinium chloride, alcohol derivatives such as chlorobutanol, phenethyl alcohol and benzyl alcohol, organic acids and salts thereof such as sodium dehydroacetate, sorbic acid and salt thereof, phenols such as p-chloromethoxyphenol and p-chloro-m-cresol, and organic mercurials such as thimerosal, phenylmercuric nitrate and nitromersol. Examples of the isotonizing agent include sodium chloride, glycerol and mannitol. Examples of the buffer include boric acid and salt thereof, phosphate, acetate and amino acid salt. Examples of the stabilizer include antioxidants such as sodium sulfite, sodium hydrogensulfite and sodium hydrogenmetasulfite, and chelating agents such as sodium edetate, citric acid and salt thereof. Examples of the thickener include polyhydric alcohols such as glycerol and macrogol, sugars such as sorbitol, mannitol and sucrose, celluloses such as methyl cellulose, sodium carboxymethylcellulose and hydroxypropylmethylcellulose, and synthetic polymer compounds such as polyvinyl alcohol, polyvinylpyrrolidone and carboxyvinyl polymer. Examples of the suspending agent include the above-mentioned celluloses, synthetic polymer compounds and polysorbates.

While the amounts of these additives vary depending on the kind of active ingredient and amount thereof, it is preferable that the composition of the ophthalmic agent be similar to the physiological condition of the eye, which is isotonized with tears. For example, the additives are contained in such a proportion that affords an osmotic pressure corresponding to that of a 0.5–2.0 w/v %, preferably 0.7–1.5 w/v %, more preferably 0.8–1.0 w/v % sodium hydrochloride solution.

When the ophthalmic composition for local administration of the present invention is prepared into an aqueous eye drop, for examle, preservatives, isotonizing agents, buffers, stabilizers and pH regulators are added. The preservative is exemplified by p-hydroxybenzoates such as methyl p-hydroxybenzoate and propyl p-hydroxybenzoate, inverted soaps such as benzalkonium chloride, benzethonium chloride, chlorhexidine gluconate and cetylpyridinium chloride, alcohol derivatives such as chlorobutanol, phenethyl alcohol and benzyl alcohol, organic acids and salts thereof such as sodium dehydroacetate, sorbic acid and salt thereof, phenols such as p-chloromethoxyphenol and p-chloro-m-cresol, and organic mercurials such as thimerosal, phenylmercuric nitrate and nitromersol; the isotonizing agent is exemplified by sodium chloride, sorbitol, mannitol and glycerol; the buffer is exemplified by phosphate, boric acid, citrate, acetate and amino acid salt; the stabilizer is exemplified by sodium edetate, sodium citrate, condensed sodium phosphate and sulfites; and the pH regulator is exemplified by hydrochloric acid, acetic acid, sodium hydroxide and phosphoric acid. A water soluble polymer compound and a surfactant can be used as appropriate to prepare the composition of the invention.

Examples of the water soluble polymer compound include cellulose derivatives, vinyl polymer compounds and polyhydric alcohols; examples of the cellulose derivative include alkyl celluloses, such as methyl cellulose and carboxymethylcellulose, and hydroxyalkylcelluloses, such as hydroxypropylmethylcellulose and hydroxyethylcellulose; examples of the vinyl polymer compound include polyvinylpyrrolidone, polyvinyl alcohol, carboxyvinyl polymer and ethylene-maleic anhydride polymer; and examples of polyhydric alcohol include polyethylene glycol and propylene glycol. The surfactant is exemplified by non-ionic surfactants, such as polysorbate and polyoxyethylene hydrogenated castor oil, cationic surfactants such as quaternary ammonium salt, anionic surfactants such as alkyl sulfate, and amphoteric surfactants such as lecithin. When the ophthalmic composition for topical application of the present invention is formulated into a gel composition, sodium alginate is used in addition to the above-mentioned preservatives and water soluble polymers. When the ophthalmic composition for topical application of the present invention is formulated into a non-aqueous composition such as an ointment, for example, liquid paraffin, propylene glycol, β-octyldodecanol, petrolatum, plastibase and vegetable oil are added besides the above-mentioned preservatives.

The ophthalmic composition of the present invention is advantageously adjusted to a pH range generally employed for eye drops, which is from 3 to 8, preferably from 4 to 6. For adjusting the pH, hydrochloric acid, acetic acid, sodium hydroxide and the like are used.

The ophthalmic composition of the present invention is advantageously adjusted to have an osmotic pressure generally employed for eye drops, which is 230–450 mOsm, preferably 260–320 mOsm. For adjusting the osmotic pressure, sodium chloride, boric acid, glycerol and mannitol are used.

The ophthalmic composition of the present invention may comprise other pharmaceutical ingredients such as a therapeutic agent for glaucoma, a therapeutic agent for cataract, an antibacterial agent, an antiallergic agent and an antiinflammatory agent. Examples of the therapeutic agent for glaucoma include pilocarpine, distigmine bromide, epinephrine dipivalate, timolol maleate and bupranolol hydrochloride. Examples of the therapeutic agent for cataract include pirenoxine and glutathione. Antibacterial agents include, for example, antibiotics such as penicillin G potassium, chloramphenicol, erythromycin, kanamycin sulfate and tetracycline hydrochloride, and antifungal agents such as pimaricin, amphotericin B and nystatin. Antiallergic agents include, for example, anti-histamic agents such as diphenhydramine and chlorpheniramine, and sodium cromoglicate. Antiinflammatory agents include, for example, adrenocortical hormones such as cortisone, prednisolone, triamcinolone acetonide, dexamethasone and betamethasone, and non-steroidal antiinflammatory agents such as indomethacin, flurbiprofen and pranoprofen.

These pharmaceutical ingredients are contained in a proportion of 0.001–100 parts by weight, preferably 0.01–50 parts by weight per part by weight of Compound (I) or a salt thereof.

The ophthalmic composition of the present invention may be formulated into a sustained release preparation. For this end, for example, a biodecomposable polymer, an acrylic resin and the like are preferably added. They are generally added in a proportion of 0.1–100 parts by weight, preferably 0.5–50 parts by weight per part by weight of Compound (I) or a salt thereof.

The ophthalmic composition of the present invention can be formulated into various dosage forms generally employed for ophthalmic agents, such as aqueous solutions, suspensions, gels, ointments, sustained release agents or the like. Alternatively, the composition of the invention may be formulated into powders, granules or tablets, which can be dissolved in purified water and the like.

For producing the composition of the present invention, any production method known per se, which is generally used for producing ophthalmic agents, can be used. For example, eye drops and eye ointments are produced according to the method described in Manual and General Rules for Preparations, The Pharmacopoeia of Japan, 12th Ed., supervised by Nikon Koteisho Kyokai and published by Hirokawa Shoten, Tokyo, Japan (1991), Tenganzai, Kenji Motose, Nanzan-do, Tokyo, Japan (1984) or The United States Pharmacopia, 23rd Ed., published by United States Pharmacopeial Convention (1995). When a sustained release preparation is desired, the method described in, for example, BIOPHARMACEUTICS OF OCULAR DRUG DELIVERY [Peter Edma ed., CRC Press, USA (1993)] can be used.

The ophthalmic composition of the present invention thus obtained has a superior local action, particularly, a superior ocular hypotensive action, causes less side effects, and is extremely low toxic. Accordingly, the composition can be used safely for the prevention and treatment of eye diseases in mammals (e.g. mice, rats, hamsters, rabbits, cats, dogs, horses, cows, sheep, monkeys and humans), such as high intraocular pressure and glaucoma, which are accompanied by increased intraocular pressure. While the use of the composition of the present invention varies depending on the dosage form, the composition can be used according to the method generally employed for known ophthalmic agents, which is exemplified by direct dropwise addition or point instillation into conjunctival sac. More specifically, the ophthalmic composition of the present invention is administered, for example, as an eye drop for treating adult glaucoma by instillation (3 to 6 times a day) of one to several drops of a 0.02–2.0 w/v %, preferably 0.05–1.0 w/v % concentration eye drop of Compound (I) or a salt thereof, though the dose is subject to changes depending on age, body weight, symptom and administration route. When the composition is used as an eye ointment, Compound (I) or a salt thereof is contained in a proportion of 0.02–2.0 weight %, preferably 0.05–1.0 weight %, and 30–100 mg of the ointment is inserted into conjunctival sac with an insertion rod 3–6 times a day.

The present invention is described in more detail by illustrative Experimental Example, Examples and Reference Examples in the following. It should be understood that these are mere exemplifications and the present invention is not limited to these examples.

The melting point in Reference Examples was determined by Yanagimoto micro melting-point measurement apparatus, unless specifically indicated. Each symbol in Reference Examples means the following.

| m | multiplet | d.d | double doublet |
|---|---|---|---|
| s | singlet | bs | broad singlet |
| d | doublet | d.t | double triplet |
| t | triplet | J | coupling constant |
| q | quartet | Hz | Herz |
| ABq | AB type quartet | DMSO | dimethyl sulfoxide |

Experimental Example

Lowering of intraocular pressure in rabbits
Method

Figure 2:
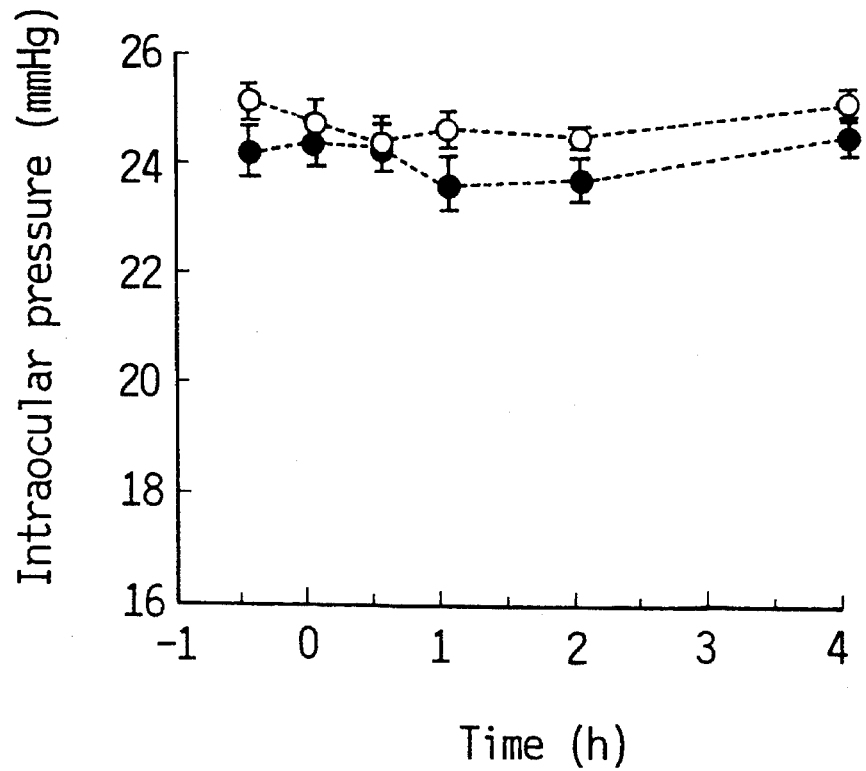
FIG. 2 is a graph showing the time-course changes in the intraocular pressure of the eye, which received instillation of physiological saline, of pigmented rabbits.

Male pigmented rabbits (6 per group) having no anterior ocular abnormalities were used. The ophthalmic composition of the present invention (Example 1, 50 µl) was instilled in one eye and changes in intraocular pressure were measured. The ocular pressure of the both eyes was measured 0.5 hour before instillation, immediately before instillation, and 0.5, 1, 2 and 4 hours after instillation, with the use of a Pneumatonograph (produced by Alcon). As a control, a vehicle (50 µl, 0.05 w/v % sodium acetate, 0.65 w/v % sodium chloride, pH 5.0) was instilled in one eye of the rabbits of the control group and physiological saline (50 µl) was instilled in the other eye.
Test results The results are shown in FIG. 1 and FIG. 2. FIG. 1 is a graph showing the time-course changes in the intraocular pressure of the eye, which received instillation of test drug, of pigmented rabbits, wherein —●— is a group which received instillation of the eye drop of Example 1, —○— is a group which received instillation of a vehicle, and each value is the mean±S.E. (n=6). The significant difference from the ocular pressure before the instillation of the test drug was $p<0.05$ in a) and $p<0.01$ in b). FIG. 2 is a graph showing the time-course changes in the intraocular pressure of the eye, which received instillation of physiological saline, of pigmented rabbits, wherein - - - ● - - - is a group which received instillation of the eye drop of Example 1, - - - ○ - - - is a group which received instillation of a vehicle, and each value is the mean± S.E. (n=6).

As a result, the eye which received instillation of a vehicle showed no change in intraocular pressure. In contrast, the eye which received instillation of the eye drop of Example showed a maximum decrease in the intraocular pressure of 4.7 mmHg one hour after the instillation, as compared with the ocular pressure immediately before the instillation, and recovered to the normal ocular pressure in four hours after the instillation (FIG. 1). On the other hand, the eye which received instillation of physiological saline showed no change in the ocular pressure for both the groups which received instillation of a vehicle or the eye drop of Example 1 in the eye. Accordingly, the ophthalmic composition of the present invention did not show an ocular pressure lowering action on the eye instilled with physiological saline (FIG. 2).

From the above-mentioned results, it is evident that the ophthalmic composition of the present invention shows a local ocular pressure lowering action.

Example 1

Eye drop

| Compound A | 1.0 g |
|---|---|
| Sodium acetate | 0.05 g |
| Sodium chloride | 0.65 g |
| Hydrochloric acid | appropriate amount |
| Distilled water | amount to make the total 100 ml |

Sodium acetate and sodium chloride were dissolved in about 80 ml of distilled water. Compound A was added and the mixture was stirred. Its pH was adjusted to 5.0 with hydrochloric acid. Distilled water was added to make the total 100 ml, whereby an eye drop suspension of 1.0 w/v % Compound A was prepared. The osmotic pressure of the eye drop was 303 mOsm.

Example 2

Eye drop

| Compound A | 0.1 g |
|---|---|
| Sodium dihydrogenphosphate | 0.1 g |
| Glycerol | 2.6 g |
| Methyl p-hydroxybenzoate | 0.003 g |
| Propyl p-hydroxybenzoate | 0.02 g |
| Sodium hydroxide | appropriate amount |
| Distilled water | amount to make the total 100 ml |

About 80 ml of distilled water was heated to about 90° C. and methyl p-hydroxybenzoate and propyl p-hydroxybenzoate were dissolved. Then, the mixture was cooled to room temperature, and Compound A, sodium dihydrogenphosphate and glycerol were dissolved. Its pH was adjusted to 6.0 with sodium hydroxide. Distilled water was added to make the total 100 ml, whereby an eye drop of 0.1 w/v % Compound A was prepared. The osmotic pressure of the eye drop was 315 mOsm.

EXAMPLE 3

Eye drop

| Compound A | 2.0 g |
|---|---|
| ε-Aminocapronic acid | 0.2 g |
| Glycerol | 1.8 g |
| Polysorbate 80 | 0.1 g |
| Sodium edetate | 0.002 g |
| Sodium hydroxide | appropriate amount |
| Distilled water | amount to make the total 100 ml |

ε-Aminocapronic acid, glycerol, polysorbate 80 and sodium edetate were dissolved in about 80 ml of distilled water. Compound A was added and the mixture was stirred. Its pH was adjusted to 5.0 with sodium hydroxide. Distilled water was added to make the total 100 ml, whereby an eye drop suspension of 2.0 w/v % Compound A was prepared. The osmotic pressure of the eye drop was 300 mOsm.

Example 4

Eye drop

| Compound A | 1.0 g |
|---|---|
| Liquid paraffin | 10.0 g |
| Methyl p-hydroxybenzoate | 0.03 g |
| Propyl p-hydroxybenzoate | 0.02 g |
| White petrolatum | amount to make the total 100 g |

Compound A, methyl p-hydroxybenzoate and propyl p-hydroxybenzoate were added to 10 g of liquid paraffin. The mixture was uniformly mixed. Then, white petrolatum was added to make the total 100 g, whereby an eye ointment of 1.0 w/w % Compound A was prepared.

Reference Example 1

A mixture of methyl 7-methoxy-3-oxo-3,4-dihydro-2H-1,5-benzoxathiepine-4-carboxylate (10 g), 3-(4-phenylpiperazin-1yl)propyl chloride (9.8 g), anhydrous potassium carbonate (6.2 g), potassium iodide (3.0 g) and methyl ethyl ketone (150 ml) was refluxed under heating for 25 hours. After cooling, inorganic matter was filtered off and the filtrate was concentrated under reduced pressure. The residue was dissolved in ethyl acetate, washed with water and dried. The solvent was evaporated under reduced pressure. The obtained residue was purified by silica gel column chromatography (eluent: hexane-ethyl acetate=3:1) to give methyl 7-methoxy-3-oxo-4-[3-(4-phenylpiperazine- 1-yl)propyl]-3,4-dihydro-2H-1,5-benzoxathiepine-4-carboxylate. Recrystallization from methanol yielded white crystals, melting point 110°–112° C., yield 2.1 g.

Elemental analysis as $C_{25}H_{30}N_2O_5S$ Calculated: C 63.81; H 6.43; N 5.95 Found : C 63.50; H 6.37; N 5.71

Reference Examples 2–3

Methyl 7-methoxy-3-oxo-3,4-dihydro-2H-1,5-benzoxathiepine-4-carboxylate was reacted with alkyl halide to give the compounds of Table 1.

TABLE 1

[Structure: benzene ring with R¹ and R² substituents, fused to S—C(COOCH₃)(X')—C(=O)—O ring]

| Ref. Ex. No. | R¹, R² | X' | Hydrochloride melting point (°C.) | Elemental analysis of hydrochloride, (figures in parentheses = calculated) C / N / H | Mass spectrum m/e |
|---|---|---|---|---|---|
| 2 | 7-CH₃O | -(CH₂)₃-N(piperidinyl-phenyl) | | 3/4 hydrate, white powder<br>60.20  2.57  6.30<br>(60.10) (2.70) (6.50) | |
| 3 | 7-CH₃O | -(CH₂)₃-N(CH₃)-CH₂-phenyl | | 1 1/2 hydrate, white powder<br>56.03  2.84  6.34<br>(56.25) (2.90) (6.25) | |

Reference Example 4

A mixture of methyl 4-(4-bromobutyl)-7-methoxy-3-oxo-3,4-dihydro-2H-1,5-benzoxathiepine-4-carboxylate (1.7 g), N-phenylpiperazine (1.37 g), potassium iodide (0.7 g), anhydrous potassium carbonate (1.2 g) and acetonitrile (30 ml) was refluxed under heating for 1.5 hours. After cooling, inorganic matter was filtered off and the filtrate was concentrated under reduced pressure. Water was added to the residue and the mixture was extracted with ethyl acetate. The organic layers were combined, washed with water and dried. The solvent was evaporated under reduced pressure. The obtained residue was purified by silica gel column chromatography (eluent: hexane-ethyl acetate=2:1) to give 1.0 g of colorless, oily methyl 7-methoxy-3-oxo-4-[4-(4-phenylpiperazin-1-yl)butyl]-3,4-dihydro-2H-1,5-benzoxathiepine-4-carboxylate. When converted to hydrochloride, a white powder was obtained, melting point 155°–165° C. (decomposition).

Elemental analysis as $C_{26}H_{32}N_2O_5S \cdot 2HCl \cdot \frac{1}{2}H_2O$ Calculated: C 55.12; H 6.22; N 4.95 Found: C 55.30; H 6.19; N 4.96

Reference Examples 5–11

In the same manner as in Reference Example 4, the compounds of Table 2 were obtained by substitution of halides with amines.

TABLE 2

[Structure: benzene ring with R¹ and R² substituents, fused to S—C(CO₂CH₃)(X')—C(=O)—O ring]

| Ref. Ex. No. | R¹, R² | X' | Hydrochloride melting point (°C.) | Elemental analysis of hydrochloride (figures in parentheses are calculated values) C / H / N | Mass spectrum m/e |
|---|---|---|---|---|---|
| 5 | 7-CH₃O | -(CH₂)₃-N(piperazinyl)-phenyl | 130–150 (decomposition) | 2HCl·1/2H₂O<br>56.00  6.41  4.81<br>(55.85) (6.54) (4.83) | |
| 6 | 7-CH₃O | -(CH₂)₆-N(piperazinyl)-phenyl | powder | 2HCl<br>57.26  6.70  4.74<br>(57.42) (6.54) (4.79) | |

TABLE 2-continued

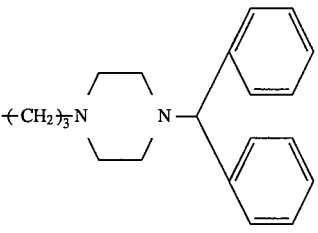

| Ref. Ex. No. | $R^1$, $R^2$ | X' | Hydrochloride melting point (°C.) | Elemental analysis of hydrochloride (figures in parentheses are calculated values) C H N | Mass spectrum m/e |
|---|---|---|---|---|---|
| 7 | 7-$CH_3O$ | —(CH₂)₃—N(piperazinyl)—CH(phenyl)₂ | oily substance (free base) | | 560 (M⁺) |
| 8 | 7-$CH_3O$ | —(CH₂)₃—N(piperazinyl)—N-(2-chlorophenyl) | oily substance (free base) | | 504, 506 (M⁺) |
| 9 | 7-$CH_3O$ | —(CH₂)₃—N(piperazinyl)—N-(2-methoxyphenyl) | oily substance (free base) | | 500 (M⁺) |
| 10 | 7-$CH_3O$ | —(CH₂)₃—N(piperazinyl)—N-(2-pyridyl) | oily substance (free base) | | 471 (M⁺) |
| 11 | 7-$CH_3O$ | —(CH₂)₃—N(CH₃)—CH₂CH₂—(2,5-dimethoxyphenyl) | oily substance (free base) | | 503 (M⁺) |

Reference Example 12

Methyl 7-methoxy-3-oxo-4-[3-(4-phenylpiperazin-1-yl)propyl]-3,4-dihydro-2H-1,5-benzoxathiepine-4-carboxylate (38 g) obtained in Reference Example 1 was dissolved in a mixed solvent of tetrahydrofuran (40 ml) and methanol (200 ml). Sodium borohydride (3.7 g) was portionwise added with stirring under ice-cooling. After the completion of the reaction, the solvent was evaporated under reduced pressure. Water was added and the mixture was extracted with ethyl acetate. The organic layers were combined, washed with water and dried. The solvent was evaporated under reduced pressure. The obtained residue was separated and purified by silica gel column chromatography (eluent: hexane-ethyl acetate-methanol=20:10:1). Colorless, oily methyl trans-3-hydroxy-7-methoxy-4-[3-(4-phenylpiperazin-1-yl)propyl]-3,4-dihydro-2H-1,5-benzoxathiepine-4-carboxylate (12 g) was obtained from the fraction eluted first.

IR spectrum (neat) cm⁻¹: 3520, 1720

NMR spectrum (CDCl₃)δ: 3.45 (3H, s, $OCH_3$), 3.60 (3H, s, $OCH_3$)

When converted to hydrochloride, a white powder was obtained.

Elemental analysis as $C_{25}H_{32}N_2O_5S \cdot 2HCl \cdot$ ғrа 1.2+ee H₂O Calculated: C 54.15; H 6.36; N 5.05 Found : C 54.27; H 6.20; N 4.89

Colorless, oily methyl cis-3-hydroxy-7-methoxy-4-[3-(4-phenylpiperazine-1-yl)propyl]-3,4-dihydro-2H-1,5-benzoxa-thiepine- 4-carboxylate (18 g) was obtained from the fraction thereafter eluted.

IR spectrum (neat) cm⁻¹: 3530, 1740

NMR spectrum (CDCl₃)δ: 3.60 (3H, s, $OCH_3$), 3.62 (3H, s, $OCH_3$)

Hydrochloride, melting point 165°–175° C. (decomposition)

Elemental analysis as $C_{25}H_{32}N_2O_5S \cdot 2HCl \cdot \frac{1}{2} H_2O$ Calculated: C 54.15; H 6.36; N 5.05 Found : C 54.02; H 6.33; N 5.00

Reference Examples 13–22

In the same manner as in Reference Example 12, the compounds obtained in Reference Examples 2–11 were reduced with sodium borohydride to give the compounds of Table 3 and Table 4.

TABLE 3

[Structure: benzene ring with R¹, R², S–X' bearing CO₂CH₃, and O– linkage, with OH group]

Configuration: 3-position OH and 4-position CO₂CH₃

| Ref. Ex. No. | R¹, R² | X' | Configuration | Hydrochloride melting point (°C.) | Elemental analysis of hydrochloride (figures in parentheses are calculated values) C / H / N |
|---|---|---|---|---|---|
| 13 | 7-OCH₃ | –(CH₂)₃–N(piperidine)–phenyl | cis + trans | powder | $C_{26}H_{33}NO_5S \cdot HCl \cdot 1/2H_2O$<br>60.37  6.89  2.64<br>(60.39) (6.82) (2.71) |
| 14 | 7-OCH₃ | –(CH₂)₃–N(CH₃)–CH₂–phenyl | cis + trans | powder | $C_{23}H_{29}NO_5S \cdot HCl \cdot 3/4H_2O$<br>57.44  6.69  2.71<br>(57.37) (6.59) (2.91) |
| 15a | 7-OCH₃ | –(CH₂)₄–N(piperazine)N–phenyl | cis | powder | $C_{26}H_{34}N_2O_5S \cdot 2HCl \cdot 1/4H_2O$<br>55.30  6.41  4.94<br>(55.36) (6.52) (4.97) |
| 15b | 7-OCH₃ | –(CH₂)₄–N(piperazine)N–phenyl | trans | carbonate 128–130 | $C_{26}H_{34}N_2O_5S \cdot H_2CO_3$<br>58.97  6.75  5.28<br>(59.10) (6.61) (5.11) |
| 16 | 7-OCH₃ | –(CH₂)₅–N(piperazine)N–phenyl | cis | powder | $C_{27}H_{36}N_2O_5S \cdot 2HCl \cdot H_2O$<br>54.81  6.81  4.73<br>(54.49) (6.95) (4.85) |
| 17 | 7-OCH₃ | –(CH₂)₆–N(piperazine)N–phenyl | cis + trans | 165–175 (free base) (112–114) | as free base: $C_{28}H_{38}N_2O_5S$<br>65.23  7.54  5.27<br>(65.34) (7.44) (5.44) |
| 18a | 7-OCH₃ | –(CH₂)₃–N(piperazine)N–CH(phenyl)₂ | cis | (free base) (133–135) | as free base: $C_{32}H_{38}N_2O_5S$<br>68.48  6.73  4.97<br>(68.30) (6.81) (4.98) |
| 18b | 7-OCH₃ | –(CH₂)₃–N(piperazine)N–CH(phenyl)₂ | trans | (free base) (173–176) | as free base: $C_{32}H_{38}N_2O_5S$<br>68.34  6.81  4.82<br>(68.30) (6.81) (4.98) |

TABLE 4

R¹, R² substituted benzoxathiepine with CO₂CH₃, X', OH groups

| Ref. Ex. No. | R¹, R² | X' | Configuration | Hydrochloride melting point (°C.) | Elemental analysis of hydrochloride (figures in parentheses are calculated values) C H N |
|---|---|---|---|---|---|
| 19a | 7-CH₃O | −(CH₂)₃−N(piperidine)−(3-chlorophenyl) | cis | 140–150 | $C_{25}H_{31}N_2O_5SCl \cdot 2HCl \cdot 3/4H_2O$<br>50.64  6.11  4.61<br>(50.59) (5.85) (4.72) |
| 19b | 7-CH₃O | −(CH₂)₃−N(piperidine)−(3-chlorophenyl) | trans | (free base)<br>(112–113) | $C_{25}H_{31}N_2O_5SCl$ (free base)<br>59.28  6.27  5.34<br>(59.22) (6.16) (5.52) |
| 20a | 7-CH₃O | −(CH₂)₃−N(piperazine)−N−(2-methoxyphenyl) | cis | powder | $C_{26}H_{34}N_2O_6S \cdot 2HCl \cdot 1\,1/2H_2O$<br>51.99  6.55  4.39<br>(51.83) (6.52) (4.65) |
| 20b | 7-CH₃O | −(CH₂)₃−N(piperazine)−N−(2-methoxyphenyl) | trans | powder | $C_{26}H_{34}N_2O_6S \cdot 2HCl \cdot H_2O$<br>52.51  6.62  4.83<br>(52.61) (6.45) (4.72) |
| 21a | 7-CH₃O | −(CH₂)₃−N(piperazine)−N−(2-pyridyl) | cis | powder | $C_{24}H_{31}N_3O_5S \cdot 2HCl \cdot 7/4H_2O$<br>49.97  6.66  7.06<br>(49.86) (6.36) (7.26) |
| 21b | 7-CH₃O | −(CH₂)₃−N(piperazine)−N−(2-pyridyl) | trans | powder | $C_{24}H_{31}N_3O_5S \cdot 2HCl \cdot 1/2H_2O$<br>51.75  5.97  7.54<br>(51.89) (6.20) (7.56) |
| 22 | 7-CH₃O | −(CH₂)₃−N(CH₃)−CH₂CH₂−(2,3-dimethoxyphenyl with OCH₃) | cis + trans | powder | $C_{26}H_{35}NO_7S \cdot HCl \cdot H_2O$<br>56.01  6.82  2.30<br>(55.76) (6.84) (2.50) |

Reference Example 23

Methyl cis-3-hydroxy-7-methoxy-4-[2-oxo-2-(4-phenylpiperazin-1-yl)ethyl]-3,4-dihydro-2H-1,5-benzoxathiepine-4-carboxylate (0.5 g) was added to a solution of sodium monoacetoxyborohydride prepared by suspending sodium borohydride (0.1 g) in 15 ml of tetrahydrofuran and dropwise adding acetic acid (0.19 g) while stirring the mixture. The mixture was refluxed under heating for 20 hours. The reaction mixture was concentrated under reduced pressure. Water was added to the residue and the mixture was extracted with ethyl acetate. The organic layer was washed with water and dried. The solvent was evaporated under reduced pressure. The obtained residue was purified by silica gel column chromatography (eluent: hexane-ethyl acetate=1:1) to give 0.2 g of colorless, oily methyl cis-3-hydroxy-7-methoxy-4-[2-(4-phenylpiperazine-1-yl)ethyl]-3,4-dihydro-2H-1,5-benzoxathiepine-4-carboxylate. When converted to hydrochloride, a white powder was obtained.

Elemental analysis as $C_{24}H_{30}N_2O_5S \cdot 2HCl \cdot 1/4\,H_2O$ Calculated: C 53.77; H 6.11; N 5.23 Found : C 53.67; H 6.19; N 5.35

Reference Example 24

Methyl cis-3-hydroxy-7-methoxy-4-[2-oxo-2-(4-phenylpiperazin-1-yl)ethyl]-3,4-dihydro-2H-1,5-benzoxathiepine-4-carboxylate (0.7 g) was added to a mixture of lithium aluminum hydride (0.24 g) and ethyl ether (50 ml), and the mixture was refluxed under heating for 2 hours. After cooling, water (0.25 ml), a 15% sodium hydroxide solution (0.25 ml) and water (0.75 ml) were sequentially added, and the mixture was stirred for 30 minutes. The resultant precipitate was filtered off and washed with ethyl acetate. The filtrate was combined and concentrated under reduced pressure. The residue was recrystallized from ethyl acetate to give 0.5 g of colorless prism crystals of cis-4-hydroxymethyl-7-methoxy-4-[2-(4-phenylpiperazin-1-yl)ethyl]-3,4-dihydro-2H-1,5-benzoxathiepin-3-ol, melting point 153°–156° C.

Elemental analysis as $C_{23}H_{30}N_2O_4S$ Calculated: C 64.16; H 7.02; N 6.51 Found : C 64.30; H 7.10; N 6.48

Reference Example 25

Methyl cis-4-diethylcarbamoylmethyl-3-hydroxy-3,4-dihydro-2H-1,5-benzoxathiepine-4-carboxylate was treated in the same manner as in Reference Example 24 to give colorless, oily cis-4-(2-diethylaminoethyl)-4-hydroxymethyl-7-methoxy-3,4-dihydro-2H-1,5-benzoxathiepin-3-ol.

IR spectrum (neat) $cm^{-1}$: 3400

NMR spectrum $(CDCl_3)\delta$: 1.00 ppm (6H, t, $2CH_3$), 1.75 (2H, m), 2.45 (6H, m), 3.58 (3H, s, $OCH_3$), 3.60 (2H, d,d, $CH_2OH$), 3.90 (2H, —O—$CH_2$—C—OH)

Reference Example 26

4-(1,3-Dioxolan-1-yl)ethyl-7-methoxy-3,4-dihydro-2H-1,5-benzoxathiepin-3-one (0.8 g) was dissolved in methanol (20 ml). Sodium borohydride was portionwise added with stirring. A 1N sodium hydroxide solution was added when the spot of the starting compound disappeared on thin-layer chromatogram and the mixture was extracted with ethyl acetate. The organic layers were combined, washed with water and dried. The solvent was evaporated under reduced pressure. Dioxane (5 ml), water (2 ml) and p-toluenesulfonic acid (40 mg) were added to the residue obtained and the mixture was stirred at room temperature for 8 hours. Water was added to the reaction mixture and the mixture was extracted with ethyl acetate. The organic layers were combined and the solvent was evaporated under reduced pressure. Acetonitrile (10 ml) and 4-phenylpiperazine (400 mg) were added to the residue and the mixture was stirred at room temperature for 20 hours. Then, sodium cyanoborohydride (200 mg) and methanol (5 ml) were added, and the mixture was stirred for 10 hours. A 1N sodium hydroxide solution was added to the reaction mixture, and the mixture was extracted with ethyl acetate. The organic layers were combined, washed with water and dried. The solvent was evaporated under reduced pressure. The obtained residue was separated and purified by silica gel column chromatography (eluent: hexane-ethyl acetate-methanol=10:10:1) to give 200 mg of colorless, oily 7-methoxy-4-[3-(4-phenylpiperazin-1-yl) propyl]-3,4-dihydro-2H-1,5-benzoxathiepin-3-ol. When converted to hydrochloride, a white powder was obtained.

Elemental analysis as $C_{23}H_{30}N_2O_3S.2HCl.½ H_2O$ Calculated: C 55.63; H 6.70; N 5.64 Found : C 55.73; H 6.61; N 5.64

Reference Example 27 cis-4-(2-Diethylaminoethyl)-4-hydroxymethyl-7-methoxy-3,4-dihydro-2H-1,5-benzoxathiepin-3-ol (0.7 g) obtained in Reference Example 25 was dissolved in pyridine (10 ml). Acetic anhydride (6 ml) was added and the mixture was allowed to stand at room temperature for 3 hours. The reaction mixture was poured into ice water and extracted with ethyl acetate. The organic layer was washed with an aqueous solution of sodium hydrogencarbonate and water, and dried. The solvent was evaporated under reduced pressure to give 0.66 g of colorless, oily cis-3-acetoxy-4-acetoxymethyl-7-methoxy-4-(2-diethylaminoethyl)-3,4-dihydro-2H-1,5-benzoxathiepine. Recrystallization of the hydrochloride of the obtained compound from ethanol-ethyl ether yielded white crystals, melting point 177°–179° C.

Elemental analysis as $C_{21}H_{31}NO_6S.HCl.⅓H_2O$ Calculated: C 54.19; H 7.01; N 3.06 Found : C 54.27; H 7.05; N 3.06

Reference Example 28

In the same manner as in Reference Example 27, the compound obtained in Reference Example 12 was acetylated to give methyl cis-3-acetoxy-7-methoxy-4-[3-(4-phenylpiperazin-1-yl)propyl]3,4-dihydro-2H-1,5-benzoxathiepine-4-carboxylate. Recrystallization from ethyl acetate-n-hexane yielded colorless prism crystals. The structure can be identified by X-ray crystal structure analysis, melting point 168°–170° C.

Elemental analysis as $C_{27}H_{35}N_2O_6S$ Calculated: C 63.01; H 6.66; N 5.44 Found : C 63.01; H 6.69; N 5.40

Reference Example 29

In the same manner as in Reference Example 24, the compound obtained in Reference Example 12 was reduced with lithium aluminum hydride to give cis-4-hydroxymethyl-7-methoxy-4-[3-(4-phenylpiperazin-1-yl)propyl]-3,4-dihydro-2H-1,5-benzoxathiepin-3-ol. Recrystallization from ethyl acetate yielded colorless needle crystals, melting point 163°–165° C.

Elemental analysis as $C_{24}H_{32}N_2O_4S$ Calculated: C 64.84; H 7.25; N 6.30 Found : C 64.76; H 7.31; N 6.39

Reference Example 30

Methyl cis-3-hydroxy-7-methoxy-4-[3-(4-phenylpiperazin-1-yl)propyl]-3,4-dihydro-2H-1,5-benzoxathiepine-4-carboxylate (160 mg) obtained in Reference Example 12 was dissolved in methanol (5 ml). 1N Sodium hydroxide (3 ml) was added and the mixture was stirred at 60° C. for 1 hour. The reaction mixture was concentrated under reduced pressure, and water (5 ml) was added to the residue. The pH was adjusted to 3 to 4 with 1N hydrochloric acid and the mixture was cooled. The resulting precipitate was collected by filtration, washed with acetone and dried to give 0.13 g of cis-3-hydroxy-7-methoxy-4-[3-(4-phenylpiperazin-1-yl)propyl]-3,4-dihydro-2H-1,5-benzoxathiepine-4-carboxylic acid as white crystals, melting point 250°–260° C. (decomposition).

Elemental analysis as $C_{24}H_{30}N_2O_5S.H_2O$ Calculated: C 60.48; H 6.77; N 5.88 Found : C 60.27; H 6.73; N 5.66

Reference Example 31

Methyl cis-3-hydroxy-7-methoxy-4-[3-(4-phenylpiperazin-1-yl)propyl]-3,4-dihydro-2H-1,5-benzoxathiepine-4-carboxylate (0.3 g) obtained in Reference Example 12 was dissolved in N,N-dimethylformamide (5 ml). Phenyl isocyanate (0.08 g) and triethylamine (0.1 ml) were added and the mixture was stirred at room temperature for 3 hours. The reaction mixture was poured into water and extracted with ethyl acetate. The organic layer was washed with water and dried. The solvent was evaporated under reduced pressure and the residue was purified by silica gel column chromatography. The portion eluted with a mixed solvent of n-hexane:ethyl acetate=3:1–1:1 was collected and evaporated under reduced pressure to give 0.4 g of colorless, oily methyl cis-7-methoxy-3-phenylcarbamoyloxy-4-[3-(4-phenylpiperazin-1-yl)propyl]-3,4-dihydro-2H-1,5-benzoxathiepine-4-carboxylate. A solution of hydrochloric acid-ethanol was added to give 0.3 g of hydrochloride as a powder.

Elemental analysis as $C_{32}H_{37}N_3O_6S\cdot 2HCl\cdot \frac{1}{2}H_2O$ Calculated: C 57.05; H 5.99; N 6.23 Found : C 56.78; H 5.96; N 6.37

Reference Example 32

Methyl 3-oxo-3,4-dihydro-2H-1,5-benzoxathiepine-4-carboxylate was condensed with 3-(4-phenylpiperazin-1-yl)propyl chloride in the same manner as in Reference Example 1 to isolate methyl 3-oxo-[3-(4-phenylpiperazin-1-yl)propyl]-3,4-dihydro-2H-1,5-benzoxathiepine-4-carboxylate as hydrochloride. Recrystallization from methanol yielded white crystals, melting point 176°–178° C.

Elemental analysis as $C_{24}H_{28}N_2O_4S\cdot HCl\cdot \frac{1}{2}H_2O$ Calculated: C 59.67; H 6.26; N 5.80 Found : C 59.49; H 6.33; N 5.79

Reference Example 33

Methyl 3-oxo-[3-(4-phenylpiperazin-1-yl)propyl]-3,4-dihydro-2H-1,5-benzoxathiepine-4-carboxylate hydrochloride obtained in Reference Example 32 was reduced with sodium borohydride in the same manner as in Reference Example 12 and separated and purified by silica gel column chromatography (eluent: hexane-ethyl acetate-methanol=10:10:1). A transcompound was obtained from the fraction eluted first and a ciscompound was obtained from the fraction eluted thereafter.

Methyl cis-3-hydroxy-4-[3-(4-phenylpiperazin-1-yl)propyl]3,4-dihydro-2H-1,5-benzoxathiepine-4-carboxylate dihydrochloride. Recrystallization from methanol-ethyl acetate yielded colorless plate crystals, melting point 196°–198° C.

Elemental analysis as $C_{24}H_{30}N_2O_4S\cdot 2HCl$ Calculated: C 55.92; H 6.26; N 5.43 Found : C 55.73; H 6.15; N 5.51

Methyl trans-3-hydroxy-4-[3-(4-phenylpiperazin-1-yl)propyl]-3,4-dihydro-2H-1,5-benzoxathiepine-4-carboxylate dihydrochloride. White amorphous powder.

Elemental analysis as $C_{24}H_{30}N_2O_4S\cdot 2HCl\cdot \frac{1}{3}H_2O$ Calculated: C 55.28; H 6.31; N 5.37 Found : C 55.29; H 6.49; N 5.11

Reference Example 34 cis-3-Hydroxy-7-methoxy-4-[3-(4-phenylpiperazin-1-yl)propyl]-3,4-dihydro-2H-1,5-benzoxathiepine-4-carboxylic acid (0.12 g) obtained in Reference Example 30 was dissolved in ethanol (3 ml). Diethyl sulfate (50 mg) and sodium hydrogencarbonate (100 mg) were added and the mixture was refluxed under heating for 3 hours. The reaction mixture was poured into water and extracted with ethyl acetate. The organic layer was washed with water and dried. The solvent was evaporated under reduced pressure and the residue was purified by silica gel column chromatography (eluent: hexane-ethyl acetate=1:1) to give 50 mg of colorless, oily ethyl cis-3-hydroxy-7-methoxy-4-[3-(4-phenylpiperazin-1-yl)propyl]-3,4-dihydro-2H-1,5-benzoxathiepine-4-carboxylate. When converted to hydrochloride, a white amorphous powder was obtained.

Elemental analysis as $C_{26}H_{34}N_2O_5S\cdot 2HCl\cdot \frac{1}{4}H_2O$ Calculated: C 55.36; H 6.52; N 4.97 Found : C 55.30; H 6.64; N 4.94

Reference Examples 35, 36

In the same manner as in Reference Example 4, the compounds of Table 5 were obtained.

TABLE 5

| Ref. Ex. No. | $R^1$, $R^2$ | X' | Hydrochloride melting point (°C.) | Elemental analysis of hydrochloride, (figures in parentheses = calculated) | | | Mass spectrum m/e |
|---|---|---|---|---|---|---|---|
| | | | | C | N | H | |
| 35 | 7-$CH_3O$ | $-(CH_2)_3-N\diagdown\diagup N-\bigcirc-OCH_3$ | (free base) (133–135) | $C_{26}H_{32}N_2O_6S\cdot \frac{1}{2}H_2O$ 60.95 (61.27) | 5.48 (5.50) | 6.30 (6.53) | 500 ($M^+$) |
| 36 | 7-$CH_3O$ | $-(CH_2)_3-N\diagdown\diagup NCH_2-\bigcirc$ | oily substance | | | | 484 ($M^+$) |

Reference Examples 37, 38

In the same manner as in Reference Example 12, the compounds of Reference Examples 35 and 36 were reduced to give the compounds of Table 6.

TABLE 6

$$\text{structure: benzene ring with } R^1, R^2 \text{ substituents, fused to S-CH(COOCH}_3\text{)-X' / CH(OH)-CH}_2\text{-O ring}$$

| Ref. Ex. No. | $R^1, R^2$ | X' | Configuration | Hydrochloride melting point (°C.) | Elemental analysis of hydrochloride, (figures in parentheses = calculated) C N H |
|---|---|---|---|---|---|
| 37a | 7-$CH_3O$ | $-(CH_2)_3-N\langle\text{piperazine}\rangle N-C_6H_4-OCH_3$ | cis | powder | $C_{26}H_{34}N_2O_6S \cdot 2HCl$ 54.56  5.05  6.29 (54.26) (4.87) (6.30) |
| 37b | 7-$CH_3O$ | $-(CH_2)_3-N\langle\text{piperazine}\rangle N-C_6H_4-OCH_3$ | trans | powder | $C_{26}H_{34}N_2O_6S \cdot 2HCl \cdot 1/2H_2O$ 53.67  4.68  6.34 (53.42) (4.79) (6.38) |
| 38a | 7-$CH_3O$ | $-(CH_2)_3-N\langle\text{piperazine}\rangle NCH_2-C_6H_5$ | cis | powder | $C_{26}H_{34}N_2O_5S \cdot 2HCl \cdot H_2O$ 54.07  4.76  6.61 (54.07) (4.85) (6.63) |
| 38b | 7-$CH_3O$ | $-(CH_2)_3-N\langle\text{piperazine}\rangle NCH_2-C_6H_5$ | trans | powder | $C_{26}H_{34}N_2O_5S \cdot 2HCl \cdot 3/4H_2O$ 54.40  4.86  6.41 (54.49) (4.89) (6.60) |

Reference Example 39

Methyl cis-4-(3-chloropropyl )-3-hydroxy-7-methoxy-3,4-dihydro- 2H-1,5-benzoxathiepine-4-carboxylate (14 g) was refluxed under heating with 4-phenylpiperazine (9.0 g), anhydrous potassium carbonate (9.0 g), potassium iodide (0.5 g) and acetonitrile (100 ml) for 20 hours. After cooling, inorganic matter was filtered off and the filtrate was concentrated under reduced pressure. The residue was dissolved in ethyl acetate. The organic layer was washed with water and dried. The solvent was evaporated under reduced pressure. The residue was purified by silica gel column chromatography (eluent: hexane-ethyl acetate-methanol:= 10:10:1) and an oil obtained was crystallized into hydrochloride to give colorless crystals of dihydrochloride of methyl cis-3-hydroxy-7-methoxy-4-[3-(4-phenylpiperazin-1-yl)propyl]-3,4-dihydro-2H-1,5-benzoxathiepine-4-carboxylate obtained in Reference Example 12, yield 8 g.

Recrystallization of the compound from 50% ethanol yielded colorless prism crystals of methyl cis-3-hydroxy-7-methoxy-4-[3-(4-phenylpiperazin-1-yl)propyl]-3,4-dihydro-2H-1,5-benzoxathiepine-4-carboxylate monohydrochloride, melting point 154°–155° C. (measured by Yanagimoto micro melting-point apparatus), melting point 132°–133° C. (decomposition, measured by the method in The Pharmacopoeia of Japan).

Elemental analysis as $C_{25}H_{32}N_2O_5S \cdot HCl \cdot 2H_2O$ Calculated: C 55.09; H 6.84; N 5.14 Found : C 55.46; H 6.77; N 5.09

IR ν max(KBr) cm$^{-1}$: 3600–3300, 1735, 1720, 1600, 1480, 1250

NMR ($d_6$-DMSO)δ: 1.3–1.8 ppm (12H), 3.68 ppm (3H, s), 3.75 ppm (3H, s), 3.8–4.3 ppm (3H), 6.7–7.4 ppm (8H)

Reference Examples 40–48

In the same manner as in Reference Example 39, the compounds of Table 7 were obtained by substitution of methyl cis-4-(3-chloropropyl)-3-hydroxy-7-methoxy-3,4-dihydro-2H-1,5-benzoxathiepine-4-carboxylate with various amines.

TABLE 7

[Structure: CH3O-substituted benzene ring connected via S and O to a 7-membered ring bearing CO2CH3, OH, and a propyl-X" substituent]

| Ref. Ex. No. | X" | Hydrochloride melting point (°C.) | Elemental analysis of hydrochloride (figures in parentheses are calculated values) C  H  N |
|---|---|---|---|
| 40 | -N(piperidine)-CH(phenyl) | powder | C26H33NO5S.HCl.1/2H2O  60.14  6.69  2.67  (60.39) (6.82) (2.71) |
| 41 | -NCH2CH2(CH3)-CH2-(2,3-dimethoxyphenyl with OCH3 groups) | powder | C26H35NO7S.HCl.1/2H2O  56.68  6.97  2.51  (56.67) (6.77) (2.54) |
| 42 | -N(piperidine)-CH-C(=O)-(4-F-phenyl) | powder | C27H32FNO6S.HCl.1/2H2O  57.38  5.80  2.40  (57.59) (5.73) (2.49) |
| 43 | -N(piperazine)N-(2-CH3-phenyl) | powder | C26H34N2O5S.2HCl  55.95  6.52  4.82  (55.81) (6.48) (5.01) |
| 44 | -N(piperazine)N-(4-F-phenyl) | 140–150 | C25H31N2O5SF.2HCl.1/2H2O  52.71  5.82  4.79  (52.44) (5.99) (4.89) |
| 45 | -N(morpholine)O | 205–210 | C19H27NO6S.HCl  52.57  6.72  3.19  (52.59) (6.50) (3.23) |
| 46 | -N(piperazine)NCH3 | (free base) 142–145 | C20H30N2O5S.1/2H2O  57.45  7.40  6.71  (57.25) (7.45) (6.68) |
| 47 | -N(C2H5)2 | 185–188 | C19H29NO5S.HCl  54.07  7.23  3.34  (54.34) (7.20) (3.34) |
| 48 | -NH-cyclopentyl | powder | C20H29NO5S.HCl.1/2H2O  54.51  7.22  3.23  (54.47) (7.09) (3.18) |

Reference Example 49

Methyl 7-methyl-3-oxo-3,4-dihydro-2H-1,5-benzoxathiepine-4-carboxylate (1.7 g) was reacted with 3-(4-phenylpiperazin-1-yl)propyl chloride in the same manner as in Reference Example 1 to give 0.9 g of colorless, oily methyl 7-methyl-3-oxo-4-[3-(4-phenylpiperazin-1-yl)propyl]-3,4-dihydro-2H-1,5-benzoxathiepine-4-carboxylate.

Mass spectrum (m/e): 454 (M$^+$)

IR spectrum ν max(neat) cm$^{-1}$: 1760, 1730 (C=O)

NMR spectrum (CDCl$_3$)δ: 2.22 (3H, s, C$_7$—CH$_3$), 3.72 (3H, s, C$_4$—COOCH$_3$), 4.62 (2H, d.d, C$_2$—H)

When converted to hydrochloride, white crystals were obtained, melting point 140°–150° C. (decomposition).

Elemental analysis as C$_{25}$H$_{30}$N$_2$O$_4$S.2HCl.½ H$_2$O Calculated: C 55.96; H 6.20; N 5.22 Found : C 56.11; H 6.19; N 5.11

Reference Example 50

In the same manner as in Reference Example 1, methyl 7-chloro-3-oxo-3,4-dihydro-2H-1,5-benzoxathiepine-4-carboxylate was reacted with 3-(4-phenylpiperazin-1-yl)propyl chloride to give methyl 7-chloro-3-oxo-4-[3-(4-phenylpiperazin-1-yl)propyl]3,4-dihydro-2H-1,5-benzoxathiepine-4-carboxylate. When converted to hydrochloride, white crystals were obtained, melting point 197°–199° C.

Elemental analysis as $C_{24}H_{27}N_2SCl.2O_4Hcl.\frac{1}{4} H_2O$ Calculated: C 52.18; H 5.38; N 5.07 Found : C 52.11; H 5.11; N 4.98

Reference Example 51

Methyl 7-methyl-3-oxo-4-[3-(4-phenylpiperazin-1-yl-)propyl]3,4-dihydro-2H-1,5-benzoxathiepine-4-carboxylate (0.9 g) was reacted in the same manner as in Reference Example 12 to give 0.3 g of colorless, oily methyl trans-3-hydroxy-7-methyl-4-[3-(4-phenylpiperazin-1-yl)propyl]-3,4-dihydro-2H-1,5-benzoxathiepine-4-carboxylate and 0.43 g of colorless, oily methyl cis-3-hydroxy-7-methyl-4-[3-(4-phenylpiperazin-1-yl)propyl]-3,4-dihydro-2H-1,5-benzoxathiepine-4-carboxylate. Trans-compound IR spectrum (neat) $cm^{-1}$: 3550(OH), 1730 (C=O)

NMR spectrum $(CDCl_3)\delta$: 2.25 (3H, s, $C_7$–$CH_3$), 3.52 (3H, s, $C_4$—$COOCH_3$)

When converted to hydrochloride, white crystals were obtained, melting point 145°–155° C.

Elemental analysis as $C_{25}H_{32}N_2O_4S.2HCl.\frac{1}{4} H_2O$ Calculated: C 56.23; H 6.51; N 5.25 Found : C 56.39; H 6.53; N 5.24 Cis-compound IR spectrum (neat) $cm^{-1}$: 3540(OH), 1740 (C=O)

NMR spectrum $(CDCl_3)\delta$: 2.35 (3H, s, $C_7$—$CH_3$), 3.75 (3H, s, $C_4$—$COOCH_3$)

When converted to hydrochloride, a white powder was obtained.

Elemental analysis as $C_{25}H_{32}N_2O_4S.1.5HCl$ Calculated: C 58.73; H 6,60; N 5.48 Found : C 58.68; H 6.96; N 5.31

Reference Example 52

In the same manner as in Reference Example 12, methyl 7-chloro-3-oxo-4-[3-(4-phenylpiperazin-1-yl)propyl]-3,4-dihydro-2H-1,5-benzoxathiepine-4-carboxylate was reduced with sodium borohydride to give cis-isomer and trans-isomer of methyl 7-chloro-3-hydroxy-4-[3-(4-phenylpiperazin-1-yl)propyl]-3,4-dihydro- 2H-1,5-benzoxathiepine-4-carboxylate. Trans-isomer When converted to hydrochloride, white crystals were obtained, melting point 150°–160° C. (decomposition).

Elemental analysis as $C_{24}H_{29}N_2O_4SCl.2HCl$ Calculated: C 52.42; H 5.68; N 5.09 Found : C 52.24; H 5.76; N 4.97 Cis-isomer When converted to hydrochloride, white crystals were obtained, melting point 205°–207° C.

Elemental analysis as $C_{24}H_{29}N_2O_4SCl.2HCl.\frac{1}{2}H_2O$ Calculated: C 51.57; H 5.77; N 5.01 Found : C 51.77; H 5.79; N 4.97

Reference Example 53

Methyl cis-4-(3-chloropropyl)-3-hydroxy-7-methyl-3,4-dihydro-2H-1,5-benzoxathiepine-4-carboxylate (0.3 g) was reacted with 4-phenylpiperidine in the same manner as in Reference Example 39 to give 0.3 g of colorless, oily methyl cis-3-hydroxy- 7-methyl-4-[3-(4-phenylpiperidin-1-yl )propyl ]-3,4dihydro-2H- 1,5-benzoxathiepine-4-carboxylate.

IR spectrum (neat) $cm^{-1}$: 3530 (OH), 1740 (C=O)

NMR spectrum $(CDCl_3 )\delta$: 2.22 (3H, s, $C_7$—$CH3$), 3.72 (3H, s $C_4$—$COOCH_3$ )

When converted to hydrochloride, a white powder was obtained.

Elemental analysis as $C_{26}H_{33}NO_4S.HCl.\frac{1}{2}H_2O$ Calculated: C 62.32; H 7.04; N 2.80 Found : C 62.41; H 7.06; N 2.70

Reference Example 54

Methyl cis-4-(3-chloropropyl)-3-hydroxy-7-methyl-3,4-dihydro-2H-1,5-benzoxathiepine-4-carboxylate was reacted with N-methyl-2-(3,4-dimethoxyphenyl)ethylamine to give methyl cis-3-hydroxy-7-methyl-4-{3-[N-methyl-2-(3,4-dimethoxyphenyl)-ethylamino]propyl}-3,4-dihydro-2H-1,5-benzoxathiepine-4-carboxylate.

When converted to hydrochloride, a white powder was obtained.
Elemental analysis as $C_{26}H_{34}NO_6S.HCl.\frac{1}{2}H_2O$ Calculated: C 58.36; H 6.97; N 2.62 Found : C 58.21; H 7.21; N 2.49

Reference Example 55

A mixture of 4-(3-chloropropyl)-7-methoxy-3,4-dihydro-2H-1,5-benzoxathiepin-3-ol (500 mg), N-phenylpiperazine (500 mg), potassium iodide (50 mg), potassium carbonate (400 mg) and N,N-dimethylformamide (10 ml) was stirred at 80° C for 8 hours. Water was added to the reaction mixture and the mixture was extracted with ethyl acetate. The organic layer was washed with water and dried over anhydrous sodium sulfate. The solvent was evaporated under reduced pressure. The residue was purified by silica gel column chromatography (eluent: hexaneethyl acetatemethanol=10:10:1), and a colorless oil obtained was converted to hydrochloride and recrystallized from methanol-acetone to give a white powder of cis 7-methoxy-4-[3(4-phenylpiperazin-1-yl)propyl]-3,4-dihydro-2H-1,5-benzoxathiepin-3-ol dihydrochloride obtained in Reference Example 26.

Elemental analysis as $C_{23}H_{30}N_2O_3S.2HCl.\frac{1}{2} H_2O$ Calculated: C 55.64; H 6.70; N 5.64 Found : C 55.95; H 6.53; N 5.47 400 MHz NMR spectrum $(d_6$-DMSO$)\delta$: 3.206 ppm (1H, m, J=8.1, 3.8, 4.6Hz, $C_4$—H), 3.776 ppm (1H, d.d, J=12.2, 8.5Hz, $C_2$—H), 4.017 ppm (1H, d., J=12.2, 3.8 Hz, $C_2$—H), 4.152 ppm (1H, d.t, J=8.5, 3.8, 3.8 Hz, $C_3$—H)

Reference Example 56

7-Methoxy-3-oxo-3,4-dihydro-2H-1,5-benzoxathiepine-4-diethylcarboxamide (1.8 g) was dissolved in ethanol (15 ml). Sodium borohydride (0.3 g) was added and the mixture was stirred for 5 hours. The reaction mixture was poured into ice-water, made acidic with dilute hydrochloric acid, and extracted with ethyl acetate. The organic layer was washed with saturated brine and dried over anhydrous sodium sulfate. The solvent was evaporated under reduced pressure. The residue was purified by silica gel column chromatography (eluent: ethyl acetatehexane=1:1) to give 1.48 g of colorless, oily 3-hydroxy-7-methoxy-3,4-dihydro-2H-1,5-benzoxathiepine-4-diethylcarboxamide.

IR ν max(neat) $cm^{-1}$: 3400, 1635

In the same manner as in Reference Example 23, the compound obtained (300 mg) was reduced with sodium monoacetoxyborohydride in a tetrahydrofuran solution, and purified by silica gel column chromatography (eluent: methylene chloridemethanol=10:1). The obtained oil was converted to hydrochloride, which was recrystallized from methanol-ethyl acetate to give 138 mg of pale yellow prism crystals of cis 4-diethylaminomethyl-7-methoxy-3,4-dihydro-2H-1,5-benzoxathiepin-3-ol hydrochloride, melting point 160°–162° C. 400 MHz NMR spectrum ($d_6$-DMSO)δ: 3.719 ppm (1H, d.d, J=12.5, 8.31Hz, C2—H), 3.819 ppm (1H, d.t, J=7.8, 3.9, 3.9Hz, $C_4$—H), 4.121 ppm (1H, d.d, J=12.5, 3.9Hz, C2-H), 4.297 ppm (1H, d.t, J=8.3, 3.9, 3.9Hz, C3—H)

Elemental analysis as $C_{15}H_{23}NO_3S·HCl$ Calculated: C 53.96; H 7.25; N 4.20 Found : C 54.11; H 7.44; N 4.13

Reference Example 57

In the same manner as in Reference Example 39, methyl cis-7-chloro-4-(3-chloropropyl)-3-hydroxy-3,4-dihydro-2H-1,5-benzoxathiepine- 4-carboxylate (0.15 g) was reacted with N-methyl-2-(3,4-dimethoxyphenyl)ethylamine to give 0.06 g of oily methyl cis-7-chloro-3-hydroxy-4-{3-[N-methyl-2-(3,4-dimethoxyphenyl)ethylamino]propyl}-3,4-dihydro-2H-1,5-benzoxathiepine-4-carboxylate. When converted to hydrochloride, a white powder was obtained.

Elemental analysis as $C_{25}H_{32}NO_6SCl·HCl·½H_2O$ Calculated: C 54.05; H 6.17; N 2.52 Found : C 54.05; H 6.04; N 2.57

Reference Example 58

Optical resolution of methyl cis-3-hydroxy-7-methoxy-4-[3-(4-phenylpiperazin-1-yl)propyl]-3,4-dihydro-2H-1,5-benzoxathiepine-4-carboxylate (±)Methyl cis-3-hydroxy-7-methoxy-4-[3-(4-phenylpiperazin-1-yl)propyl]-3,4-dihydro-2H-1,5-benzoxathiepine-4-carboxylate (1.3 g) and S-(+)-1,1'-binaphthyl-2,2'-diylhydrogenphosphate (1.0 g) were dissolved in methanol (50 ml) and the mixture was concentrated under reduced pressure. The residue was dissolved in acetone-methanol and left standing overnight in a refrigerator. The resultant precipitate was collected by filtration. The obtained crystals were recrystallized three times from acetone-methanol to give white crystals.

$[α]_D^{25}$+175.5° (c=1.01, in methanol)

The obtained compound was suspended in methylene chloride. 1N Sodium hydroxide was added and the mixture was shaken. The organic layer was washed with 1N sodium hydroxide and water, and dried over anhydrous sodium sulfate. The solvent was evaporated under reduced pressure. A colorless oil obtained was dissolved in ethanol and dilute hydrochloric acid was added. The solvent was evaporated under reduced pressure. The residue was treated with methanol-ether to give (–) methyl cis-3-hydroxy-7-methoxy-4-[3-(4-phenylpiperazin-1-yl)propyl]-3,4-dihydro-2H-1,5-benzoxathiepine-4-carboxylate dihydrochloride as a white powder.

$[α]_D$–102.0° (c=0.54, in methanol)
Elemental analysis as $C_{25}H_{32}N_2O_5S·2HCl·½H_2O$ Calculated: C 54.15; H 6.36; N 5.05 Found : C 53.98; H 6.18; N 4.83

Reference Example 59

In the same manner as in Reference Example 58, a salt of (±) methyl cis-3-hydroxy-7-methoxy-4-[3-(4-phenylpiperazin-1-yl)propyl]-3,4-dihydro-2H-1,5-benzoxathiepine-4-carboxylate and R-(-)-1,1'-binaphthyl-2,2'-diylhydrogenphosphate were recrystallized three times from acetone-methanol to give white crystals of $[α]_D^{25}$–172° (c=1.03 in methanol). The obtained salt was treated with 1N-sodium hydroxide and converted to hydrochloride to give (+) methyl cis-3-hydroxy-7-methoxy-4-[3-(4-phenylpiperazine-1-yl)propyl]-3,4-dihydro-2H-1,5-benzoxathiepine-4-carboxylate hydrochloride as a white powder.

$[α]_D$+110.8° (c=0.48, in methanol)
Elemental analysis as $C_{25}H_{32}N_2O_5S·2HCl·½H_2O$ Calculated: C 54.15; H 6.36; N 5.05 Found : C 54.11; H 5.93; N 4.80

Reference Example 60

A mixture of cis-3-acetoxy-4-(3-chloropropyl)-7-methoxy-3,4-dihydro-2H-1,5-benzoxathiepine-4-N-benzylcarboxamide (0.3 g), N-phenylpiperazine (0.13 g), potassium iodide (0.1 g), potassium carbonate (0.12 g) and N,N-dimethylformamide (4 ml) was stirred at 70° C. for 2 hours. The reaction mixture was poured into ice-water (20 ml) and extracted with ethyl acetate. The extract was washed with water and dried over anhydrous sodium sulfate. The solvent was evaporated under reduced pressure. The residue obtained was treated with ethyl acetate- n-hexane to give 97 mg of cis-3-acetoxy-7-methoxy-4-[3-(4- phenylpiperazin-1-yl)propyl]-3,4-dihydro-2H-1,5-benzoxathiepine4-N-benzylcarboxamide as crystals, melting point 178–180° C. (recrystallization from ethyl acetate yielded a white powder).

Mass spectrum m/e 589($M^+$)

Elemental analysis as $C_{33}H_{39}N_3O_5S·¼H_2O$ Calculated: C 66.70; H 6.70; N 7.07 Found : C 66.75; H 6.63; N 6.87

The ophthalmic composition for local administration of the present invention has an intraocular pressure lowering action by the administration at a local site in the eye. Accordingly, the composition is advantageously used for the prevention and treatment of eye diseases such as high ocular pressure and glaucoma, which are accompanied by increased ocular pressure.

We claim:

1. A method for lowering intraocular pressure, comprising topically administering to the eye of a subject in need of such treatment a pharmaceutically effective amount of a compound of the formula

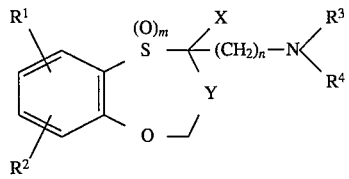

wherein $R^1$ and $R^2$ are each a hydrogen, a halogen, a hydroxyl, a lower alkyl or a lower alkoxy, $R^3$ and $R^4$ are each a hydrogen, an optionally substituted lower alkyl, an optionally substituted cycloalkyl or an optionally substituted aralkyl, or form, together with the adjacent nitrogen atom, an optionally substituted ring, X is a hydrogen, an optionally substituted lower alkyl, an optionally substituted aryl or an optionally esterified or amidized carboxyl, Y is >C=O or >CH—$OR^5$ wherein $R^5$ is a hydrogen, an acyl or an optionally substituted carbamoyl, m is an integer of from 0 to 2, and n is an integer of from 1 to 6, or a pharmaceutically acceptable salt thereof.

2. The method of claim 1, wherein the compound is of the formula

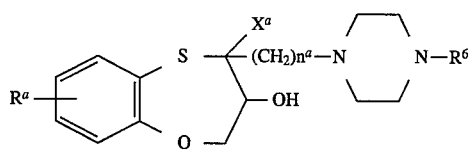

wherein $R^6$ is an optionally substituted phenyl, $R^a$ is a lower alkoxy, $X^a$ is a lower alkoxycarbonyl and $n^a$ is an integer of from 2 to 4, or a pharmeceutically acceptable salt thereof.

3. The method of claim 2, wherein the lower alkoxy is methoxy.

4. The method of claim 2, wherein the lower alkoxycarbonyl is methoxycarbonyl.

5. The method of claim 2, wherein $R^6$ is a phenyl.

6. The method of claim 2, wherein $n^a$ is 3.

7. The method of claim 1, wherein the compound is methyl cis-3-hydroxy-7-methoxy-4-[3-(4-phenyl-1-piperazinyl)propyl]-3,4-dihydro-2H-1,5-benzoxathiepine-4-carboxylate or a pharmaceutically acceptable salt thereof.

* * * * *

UNITED STATES PATENT AND TRADEMARK OFFICE
CERTIFICATE OF CORRECTION

PATENT NO. : 5,538,974
DATED : July 23, 1996
INVENTOR(S) : TAKAHIRO OGAWA and TAKAAKI DEGUCHI It is certified that error appears in the above-indentified patent and that said Letters Patent is hereby corrected as shown below:

On the cover page, section "[73]" correct the name of the assignee to read --SENJU PHARMACEUTICAL CO., LTD.--.

Signed and Sealed this

Eighth Day of April, 1997

Attest:

BRUCE LEHMAN

*Attesting Officer*     Commissioner of Patents and Trademarks